(12) United States Patent
Schmitt (10) Patent No.: US 8,798,718 B2
(45) Date of Patent: Aug. 5, 2014

(54) METHOD AND APPARATUS TO GENERATE ANGIOGRAPHIC MAGNETIC RESONANCE IMAGES (75) Inventor: Peter Schmitt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 483 days.

(21) Appl. No.: 13/085,582

(22) Filed: Apr. 13, 2011

(65) Prior Publication Data
US 2011/0251477 A1 Oct. 13, 2011

(30) Foreign Application Priority Data

Apr. 13, 2010 (DE) .......... 10 2010 003 895

(51) Int. Cl.
A61B 5/055 (2006.01)

(52) U.S. Cl.
USPC ............ 600/419; 600/413; 324/306; 324/309

(58) Field of Classification Search
USPC ........... 600/410, 413, 419; 324/306, 307, 309
See application file for complete search history.

(56) References Cited

U.S. PATENT DOCUMENTS 6,198,960 B1  3/2001 Fain et al.
6,320,377 B1 11/2001 Miyazaki et al.
2003/0220560 A1 11/2003 Kuehn
2004/0051527 A1  3/2004 Mugler, III et al.
2008/0278159 A1 11/2008 Park
2010/0280357 A1* 11/2010 Bi et al. .................. 600/419

OTHER PUBLICATIONS

"Analysis and Reduction of the Transient Response in SSFP Imaging", D. G. Nishimura et al., Proc. Intl. Soc. Mag. Reson. Med. 8 (2000) p. 301.
"Non-contrast Enhanced Three-dimensional MR Digital Subtraction Angiography at a Temporal Resolution of 100 msec.", M. Hori et al., Proc. Intl. Soc. Mag. Reson. Med. 17 (2009) p. 3257.
"Non-contrast-enhanced 4D Intracranial MR Angiography with 4D NATIVE TrueFISP", X. Bi et al., Proc. Intl. Soc. Mag. Reson. Med. 17 (2009) p. 3258.

(Continued)

Primary Examiner — Ruth S Smith
(74) Attorney, Agent, or Firm — Schiff Hardin LLP (57) ABSTRACT In a magnetic resonance system and operating method, a series with a predetermined number of flip angles is established, that begins with a first flip angle that is smaller than the last flip angle of the series, and an arbitrary flip angle is greater than or equal to the preceding flip angle in the series. Respective predetermined regions of k-space are acquired that form first and second magnetic resonance data. Using a gradient echo sequence, each region is acquired during time interval as a series of components respectively with different flip angles in the series of flip angles. Each of the angiography magnetic resonance images has a flip angle range assigned thereto, and is formed by combining respective regions of k-space filled with components of the first and second magnetic resonance data that were acquired in that range.

16 Claims, 9 Drawing Sheets

(56) References Cited

OTHER PUBLICATIONS

"Comparison of High Temporal Resolution 2D Time Resolved Blood Bolus tagging MRA and 3D Time Resolved Contrast Enhanced MRA for the Assessment of Hemodynamics in Patients with Cerebral Arteriovenous Malformations", Essig et al., Proc. Intl. Soc. Mag. Reson. Med. 17, p. 3263 (2009).

"Non-contrast-enhanced 4D Intracranial MR Angiography: Optimizations Using a Variable Flip Angle Approach", P. Schmitt et al.

"20$^{th}$ MR Angiography Workshop", MR-Angioclub Graz p. 1-132 (2008).

"Signal Targeting with Alternating Radiofrequency (STAR) Sequences: Application to MR Angiography", Robert R. Edelman et al., Magn. Reson. Med. 31, pp. 233-238 (1994).

"Quantification of Relative Cerebral Blood Flow Change by Flow-Sensitive Alternating Inversion Recovery (FAIR) Technique: Application to Functional Mapping", Seong-Gi Kim, Magn Reson Med 34, pp. 293-301 (1995).

"Optimization of Signal Behavior in the Transition to Driven Equilibrium in Steady-State Free Precession Sequences", Jürgen Henning et al., Magnetic Resonance on Medicine 48, pp. 801-809 (2002).

"Reduction of Transient Signal Oscillations in True-FISP Using a Linear Flip Angle Series Magnetization Preparation", Vibhas S. Deshpande et al, Magnetic Resonance in Medicine 49, pp. 151-157 (2003).

"A Simple Geometrical Description of the TrueFISP Ideal Transient and Steady-State Signal", Schmitt et al., Magnetic Resonance in Medicine 55, pp. 177-185 (2006).

"The Effects of Linearly Increasing Flip Angles on 3D Inflow MR Angiography", Nägele T. et al., In: Magnetic Resonance in Medicine, Academic Press 1994, vol. 31, Nr. 5, S. pp. 561-566 (1994).

* cited by examiner

METHOD AND APPARATUS TO GENERATE ANGIOGRAPHIC MAGNETIC RESONANCE IMAGES

BACKGROUND OF THE INVENTION

1. Field of the Invention

The present invention concerns a method and a magnetic resonance system to generate a series of temporally successive angiographic magnetic resonance images of an examination region, in particular a contrast agent-free generation of temporally successive angiographic magnetic resonance images.

2. Description of the Prior Art

Various methods for contrast agent-free dynamic magnetic resonance angiography, what is known as non-contrast enhanced (NCE) magnetic resonance angiography, are known in the prior art. In these methods, blood flowing in is marked with the aid of what is known as a spin labeling method and imaged during the inflow into an examination region, known as an imaging volume of interest (VOI).

To mark and depict the inflowing blood, the same examination region is typically acquired twice with different labeling. In the prior art the methods FAIR (Flow-Sensitive Alternating Inversion Recovery) and STAR (Signal Targeting with Alternating Radio Frequency Sequences) are known in this regard. In the FAIR method a first measurement is implemented in a first measurement after a selective inversion (marking) of the VOI and a second measurement is implemented after a non-selective inversion of VOI and the surrounding region. In the STAR method a region outside of the VOI from which blood flows into the VOI is inverted before a first measurement, and a second measurement occurs without marking. In both methods inflowing magnetization portions in the individual measurements respectively show a different signal and therefore can be represented by a subsequent calculation of the difference of the first measurement and the second measurement, while static regions respectively respond identically, and this static measurement signals are largely eliminated by the subtraction. In this method an image is typically respectively acquired after a specific inflow time. These methods can be used for NCE magnetic resonance angiography by repetition with different inflow times. In order to improve the efficiency of the method, an entire desired observation period of time after the marking can be scanned with a series of images (known as frames) in order to thus acquire the workflow of the inflow process with time resolution. Gradient echo methods can be used for this, for example FLASH imaging (Fast Low Angle Shot) or FISP or, respectively, TrueFISP imaging (Fast Imaging with Steady State Precession, also known as b-SSFP (Balanced Steady State Free Precession)).

In such a continuous scanning of the inflow process, the chronological development of the magnetization (and therefore of the signal) is significantly affected by the permanently active measurement. The marking—i.e. the difference between the signal values of the inflowing blood in the two measurements—disappears with time, such that the blood signal is always weaker in the difference data. Vessels that only fill late with the marked blood after the marking are thereby not (or are only insufficiently) acquired and shown. This loss of the marking takes place particularly quickly in FLASH imaging, but also represents a severe limitation in FISP imaging (Fast Imaging with Steady State Recession).

In the prior art the "marking edge" is therefore placed near to the vessels of interest in order to acquire the inflowing blood as well as possible in these regions. However, the volumes within which the inflow process can be acquired is hereby strongly limited. This is critical in the examination of pathologies with unclear flow relationships (for example the examination of arterio-venous malformations) in which it is precisely the question of vessels leading to and away that should be clarified.

SUMMARY OF THE INVENTION

An object of the present invention is to provide an improved method to generate a magnetic resonance angiography given a continuous scanning of the inflow process.

The present invention is a method to generate a series of temporally successive angiographic magnetic resonance images of an examination region. The series includes a predetermined first number of temporally successive angiographic magnetic resonance images. In the method a series is established with a predetermined second number of flip angles that can be arranged by means of an index in the series, for example. The first flip angle at the beginning of the series is smaller than the last flip angle at the end of the series, and an arbitrary flip angle within the series is essentially greater than or equal to the flip angle preceding in the series. Furthermore, first magnetic resonance data are determined by acquiring a predetermined third number of first partial segments (or regions) of k-space belonging to the first magnetic resonance data. Each partial segment of the first partial segments is acquired over a respective first time interval and respectively has a series with the second number of components. Each component is acquired according to a gradient echo method with a flip angle which exists at a position in the series of flip angles, which position corresponds to the component. At the beginning of the first time interval a fluid flowing into the examination region has a first predetermined spin marking. Second magnetic resonance data are additionally determined by acquiring a predetermined fourth number of second partial segments of k-space belonging to the second magnetic resonance data. Each partial segment of the second partial segments is acquired over a respective second time interval and has a series with the second number of components. Each component is acquired according to a gradient echo method with a flip angle which exists at a position in the series of flip angles, which position corresponds to the component. At the beginning of the second time interval, a fluid flowing into the examination region has a second predetermined spin marking that is different than the first spin marking. For each angiographic magnetic resonance image a contiguous flip angle index range is respectively established from the series of flip angles. The series of temporally successive angiographic magnetic resonance images of the examination region is generated in that a portion of the first magnetic resonance data and a portion of the second magnetic resonance data are respectively combined with one another to generate one of the angiographic magnetic resonance images. The portion of the first magnetic resonance data thereby comprises components of the first partial segments that were acquired with flip angles of the flip angle index range for the respective angiographic magnetic resonance image. The portion of the second magnetic resonance data thereby comprises components of the second partial segments that were acquired with flip angles of the flip angle index range for the respective angiographic magnetic resonance image.

The second number—thus the number of flip angles—can be selected larger than the first number (thus the number of angiographic magnetic resonance images), whereby a continuous curve of the flip angles during the acquisition and at the same time a high resolution of the magnetic resonance images can be achieved. Alternatively, the first and second numbers can be selected to be equal, i.e. each magnetic resonance image is determined with precisely one flip angle.

For example, the first and the second predetermined spin marking can be implemented with the aid of a selective inversion and a non-selective inversion (FAIR method). The examination region of interest is thereby respectively selectively inverted at the beginning of the first time intervals, for example, such that the inflowing fluid (for example inflowing blood) has no spin marking. The first predetermined spin marking in this case corresponds to a "non-marking" or "no marking". In contrast to this, at the beginning of the second time interval a non-selective inversion is implemented in both the examination region of interest and in a surroundings of the examination region of interest, such that the inflowing fluid has the spin marking produced by the inversion. The second predetermined spin marking in this case corresponds to the marking produced by the inversion. Additional marking methods known in the prior art can likewise be used, for example the aforementioned STAR method. Given a use of the STAR method, the first predetermined spin marking corresponds to a marking produced by the inversion of the surroundings while the second predetermined spin marking in this case corresponds to a "non-marking".

With the method described above, the flip angles are increased monotonically from smaller to larger values in the acquisition of temporally successive angiographic magnetic resonance images over the course of the inflow process of a fluid (for example blood) into the examination region. In an exemplary use of the STAR method, at the beginning of the first time intervals in which the fluid flowing into the examination region has a spin marking the relatively large magnitude of the fresh inflowing magnetization is therefore utilized to obtain a sufficient signal even with a relatively small flip angle. A small flip angle is accompanied by a large effective time constant, i.e. the apparent relaxation time runs very close to the true T1. The relaxation is thus relatively less additionally accelerated and the marking is only slightly attenuated via the acquisition with small flip angle. In contrast to this, larger flip angles are used at a later point in time within the first intervals, whereby the development of the magnetization (in particular in TrueFISP imaging) is moved in the direction of an optimally high value. A larger difference between the first and second magnetic resonance data—in particular at later points in time within the time intervals after the spin marking—is thus obtained for the freshly inflowing fluid. The influence of the marking of the inflowing fluid is kept low by the small flip angles to acquire the magnetic resonance data at the beginning of the intervals. The signal level of the inflowing fluid at the end of the time intervals can be kept to higher values due to the larger flip angles at the end of the time intervals. A relatively uniform difference between the marked fluid in the first magnetic resonance data and the unmarked fluid in the second magnetic resonance data can thereby be achieved.

In the acquisition of the first magnetic resonance data, multiple first partial segments of k-space belonging to the first magnetic resonance data are acquired in different first time intervals. Different partial segments of k-space are at least partially acquired in each of these multiple acquisitions. The first magnetic resonance data are subsequently generated by a combination of the multiple first partial segments. To acquire the second magnetic resonance data, multiple second partial segments of k-space belonging to the second magnetic resonance data are likewise acquired in multiple different second time intervals. In each of the multiple acquisitions at least partially different second partial segments of k-space are acquired, and the second magnetic resonance data are generated via a combination of the multiple second partial segments. Only partial segments of k-space of the corresponding magnetic resonance data are thus acquired. This process is repeated for the missing segments until the magnetic resonance data required to reconstruct a series of magnetic resonance images are present. A correspondingly short period of time within the corresponding time interval can thus be assigned to each magnetic resonance image, such that a relatively high, predetermined first number of temporally successive magnetic resonance images can also be generated with high quality for a short time interval.

In the gradient echo method the flip angle is used in order to define an excitation angle by which the negative magnetization is rotated or flipped via the application of a radio-frequency excitation pulse at the Larmor frequency. The rotation axis is thereby oriented perpendicular to the direction of the basic magnetic field. In a gradient echo method, flip angles between 0° and 90° are typically used, also 120° or more in part in TrueFISP. According to one embodiment of the present invention, a value of a flip angle in the series of flip angles is proportional to the square of its position in the series of flip angles. For example, the first flip angle at the beginning of the series can be in a range from 10-20° (advantageously 12°), and the last flip angle at the end of the series can be in a range from 30-60° (advantageously 45°), for example. For example, in magnetic resonance angiography a difference value between marked blood and unmarked blood can thereby be kept nearly constant over a time interval of approximately one second.

The predetermined third number of first partial segments and the predetermined fourth number of second partial segments can be equal. First and second magnetic resonance data thereby result with the same resolution, so the combination of the first and second magnetic resonance data into the series of angiographic magnetic resonance images is simplified.

According to one embodiment, the predetermined third number of first partial segments and the predetermined fourth number of second partial segments are acquired with temporal interleaving. Alternatively, the predetermined third number of first partial segments are acquired in a temporally contiguous manner, and the predetermined fourth number of second partial segments are acquired in a temporally contiguous manner before or after this.

According to one embodiment, the first magnetic resonance data are acquired in total in only one first time interval, meaning that the first magnetic resonance data are acquired without segmentation and the predetermined third number of first partial segments therefore has a value of one in this case. The second magnetic resonance data can likewise be acquired in total in only one second time interval, meaning that the second magnetic resonance data are acquired without segmentation and the predetermined fourth number of second partial segments therefore has a value of one in this case.

According to one embodiment, the combination of the portion of the first magnetic resonance data and the portion of the second magnetic resonance data to generate one of the angiographic magnetic resonance images comprises the following steps:

the portion of the first magnetic resonance data is transformed from k-space into image space in order to obtain a first magnetic resonance image. The portion of the second magnetic resonance data is transformed from k-space into image space in order to obtain a second magnetic resonance image. A difference image which is associated with the corresponding angiographic magnetic resonance image is determined from the first and second magnetic resonance image.

According to a further embodiment, the combination of the portion of the first magnetic resonance data and the portion of the second magnetic resonance data to generate one of the angiographic magnetic resonance images includes the following steps:

difference magnetic resonance data are formed via a complex subtraction of the portion of the first magnetic resonance data and the portion of the second magnetic resonance data in k-space. The difference magnetic resonance data are transformed from k-space into image space, and the magnetic resonance image that is thus obtained is associated with the corresponding angiographic magnetic resonance image.

According to a further embodiment, the combination of the portion of the first magnetic resonance data and the portion of the second magnetic resonance data to generate one of the angiographic magnetic resonance images comprises the following steps:

the portion of the first magnetic resonance data and the portion of the second magnetic resonance data are sorted in an interleaved manner in hybrid k-space. The interleaved magnetic resonance data are transformed from hybrid k-space into image space, and a partial region of the transformed magnetic resonance data is associated with the corresponding angiographic magnetic resonance image.

According to a further embodiment, the first and second time intervals are synchronized with heartbeats or with a phase of a heartbeat of a patient to be examined. Since in particular the arterial blood flow is pulsatile in nature, the flow velocities of the blood can change significantly over the heartbeat interval given an angiography of arterial vessels. In that the first and second time intervals are adapted to the heartbeat (for example with the aid of an EKG triggering) and thus the spin marking of the inflowing blood or of the examination region is also adapted to the heartbeat, each of the temporally successive angiographic magnetic resonance images can correspond to a specific phase of the heartbeat interval. For this the components of the partial segments of the first and second magnetic resonance data are advantageously acquired at predetermined and (for example) equidistant points in time in the first or second time intervals.

According to a further embodiment, each of the temporally successive angiographic magnetic resonance images comprises a three-dimensional data set of the examination region. The first and second magnetic resonance data consequently also comprise a three-dimensional data set of the examination region. From this a temporally dynamic three-dimensional representation of flow relationships in vessels of the examination region can be depicted with suitable presentation means, for example. For example, the MIP method (maximum intensity projection) known in the prior art can be used to clearly depict the vessels in these angiography data.

According to a further embodiment, each magnetic resonance image of the temporally successive angiography magnetic resonance images (and accordingly the first and second magnetic resonance data) can respectively comprise a two-dimensional data set of the examination region. The use of two-dimensional data sets can in particular be of use when simple vessel structures are suitably present in the corresponding two-dimensional slice plane. The primary advantage in comparison to the acquisition of a three-dimensional data set lies in the lower amount of data that is necessary, whereby fewer partial segments are required and thus the total measurement time can be shorter.

According to a further embodiment, each magnetic resonance image of the temporally successive angiographic magnetic resonance images—and therefore also the first and second magnetic resonance data—is acquired with the aid of a non-Cartesian scan. In particular, in non-Cartesian scanning a subsampling is possible due to the redundancy in temporally successive scanning, and thus a faster scanning overall can be achieved, whereby the complete imaging can be accelerated. Exemplary non-Cartesian scan patterns are: three-dimensional radial scanning ("3D Radial") in which each echo represents a projection through the k-space center; cylindrical scanning ("Stack of Stars") in which a stack of two-dimensional radial signals is acquired and the third dimension (partition direction) is coded by means of phase coding gradients; or spiral-shaped trajectories.

Due to the different spin markings of the fluid flowing into the examination region at the beginning of the first and second time intervals, the temporally successive angiographic magnetic resonance images can be generated independent of a contrast agent administration. The entire process of imaging thus can be simplified and an exposure for the patient can be reduced.

For example, the FLASH gradient echo method known in the prior art or the TrueFISP gradient echo method in a higher equilibrium (steady) state for the transverse magnetization of fluids is achieved are suitable as gradient echo methods.

Furthermore, according to the present invention a magnetic resonance system is provided to generate a series of temporally successive angiographic magnetic resonance images of an examination region. The series of temporally successive angiographic magnetic resonance images has an ordered sequence of a predetermined first number of magnetic resonance images. The magnetic resonance system comprises a control unit which is designed to establish a series with a predetermined second number of flip angles. The first flip angle at the beginning of the series is smaller than the last flip angle at the end of the series, and an arbitrary flip angle within the series is essentially greater than or equal to the preceding flip angle in the series. Furthermore, the control unit is designed to determine first magnetic resonance data by acquiring a predetermined third number of first partial segments of k-space belonging to the first magnetic resonance data. Each partial segment of the first partial segments is acquired over a respective first time interval and respectively has a series with the second number of components. Each component is acquired according to a gradient echo method with a flip angle which is present at a position in the series of the flip angles, which position corresponds to the component. At the beginning of the first time intervals, a fluid flowing into the examination region has a first predetermined spin marking. The control unit is additionally designed to determine second magnetic resonance data via acquisition of a predetermined fourth number of second partial segments of k-space belonging to the second magnetic resonance data. Each partial segment of the second partial segments is acquired over a respective second time interval and has a series with the second number of components. Each component is acquired according to a gradient echo method with a flip angle which is present at a position in the series of the flip angles, which position corresponds to the component. At the beginning of the second time interval, a fluid flowing into the examination region has a second predetermined spin marking that is different than the first spin marking. For each angiographic magnetic resonance image, the control unit respectively establishes a contiguous flip angle index range from the series of flip angles. The control unit generates the series of temporally successive angiographic magnetic resonance images of the examination region in that, to generate one of the angiographic magnetic resonance images, it combines a respective portion of the first magnetic resonance data and a respective portion of the second magnetic resonance data with one another. The portion of the first magnetic resonance data thus includes components of the first partial segments which were acquired with flip angles of the flip angle index range for the respective angiographic magnetic resonance image. The portion of the second magnetic resonance data thus includes components of the second partial segments which were acquired with flip angles of the flip angle index range for the respective angiographic magnetic resonance image.

The magnetic resonance system can be designed to implement the method described in the preceding. The magnetic resonance system therefore has the same advantages as the method described in the preceding.

The designations "first time intervals" and "second time intervals" do not represent a limitation with regard to the chronological workflow. The second magnetic resonance data can therefore also be acquired before the first magnetic resonance data. Furthermore, the first and second magnetic resonance data can also be acquired essentially simultaneously in that the first partial segments and the second partial segments are acquired in an interleaved or alternating manner. Possible methods to implement the first and second spin marking can be analogous to FAIR or STAR, for example, wherein the acquisition of the magnetic resonance data takes place with flip angles variable over time.

The present invention furthermore encompasses a computer program product (in particular a software) that can be loaded into a memory of a programmable control unit of a magnetic resonance system. All previously described embodiments of the method according to the invention can be executed with program means if the computer program product is executed in the magnetic resonance system.

The present invention encompasses an electronically readable non-transitory data medium—for example a CD or DVD—on which are stored electronically readable control information, in particular software. When this control information is read by the data medium and stored in a programmable controller of the magnetic resonance system, all embodiments of the previously described method according to the invention can be implemented with the magnetic resonance system.

DESCRIPTION OF THE PREFERRED EMBODIMENTS

Figure 1:
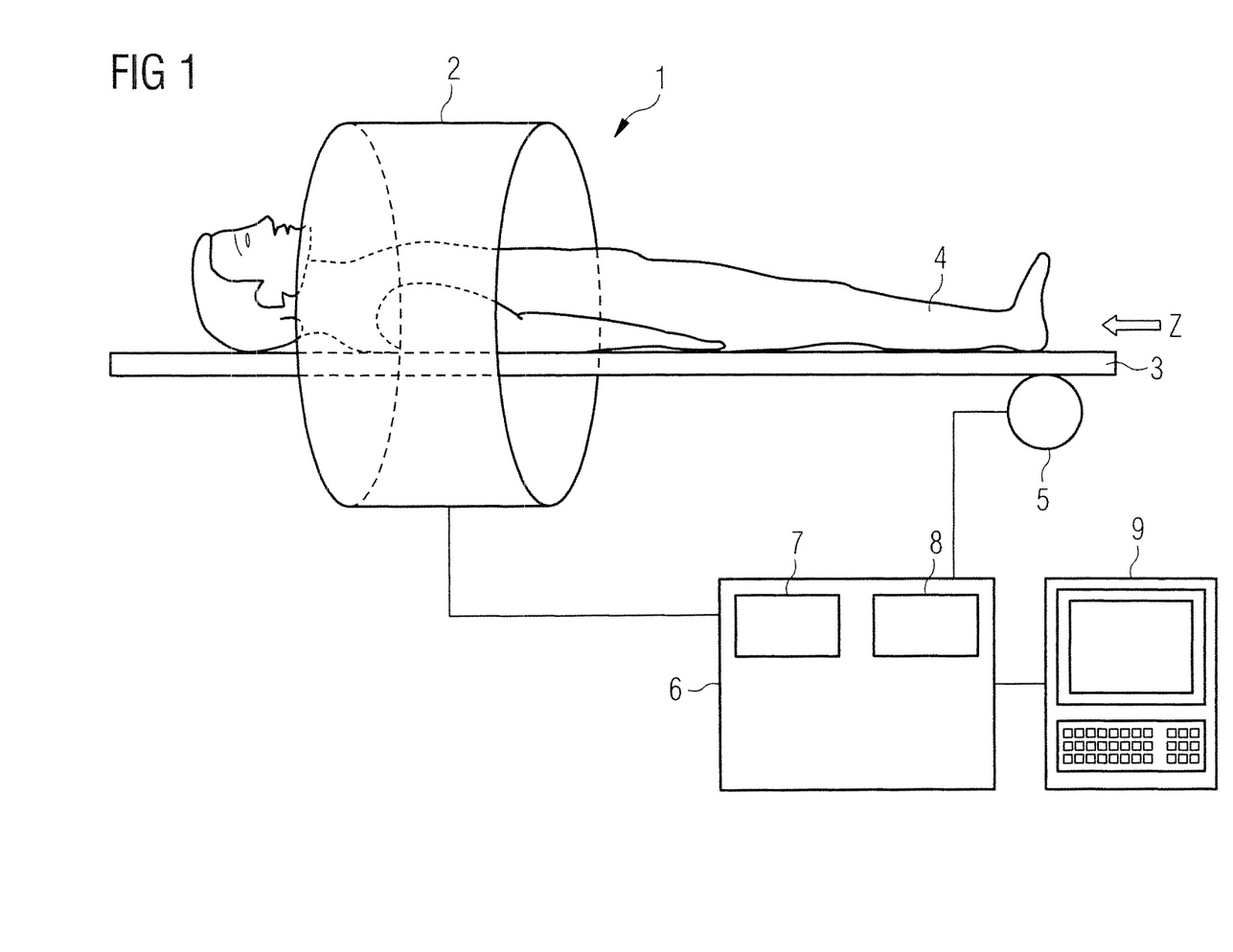
FIG. 1 schematically shows a magnetic resonance system to generate a series of temporally successive angiographic magnetic resonance images according to one embodiment of the present invention.

FIG. 1 shows a magnetic resonance system 1 with which a series of temporally successive angiographic magnetic resonance images can be generated according to the invention and which achieves an improved image quality across the entire series with a higher contrast vessel representation. The magnetic resonance system 1 has a magnet 2 to generate a polarization field B0. An examination subject 4 arranged on a bed 3 is driven with the aid of a drive 5 into the middle of the magnet 2, where an acquisition of the magnetic resonance signals from an examination region is conducted by radiating radio-frequency pulses and switching gradients. How magnetic resonance images can be generated in a pulse sequence via a series of radio-frequency pulses and switching of gradients is basically familiar to the man skilled in the art and is not described in detail here.

The magnetic resonance system 1 is connected with a central control unit 6 with which the magnetic resonance system 1 is controlled. The central control unit 6 has, among other things, a radio-frequency control unit 7 which controls the switching of the radio-frequency pulses to deflect the magnetization. A magnetic field gradient coil unit 8 controls the switching of the magnetic field gradients for spatial coding of the excited spins. The control unit 6 controls the workflow of the gradient switching, the radio-frequency pulses and the signal readout depending on the selected imaging sequence. A magnetic resonance image computer 9 calculates magnetic resonance images (as is known) via Fourier transformation from the magnetic resonance signals detected with a coil (not shown), which magnetic resonance images can be displayed on a display unit of the image computer 9. With the aid of an operating unit of the image computer 9, the magnetic resonance system 1 can be controlled by an operator. Additional typical components of a magnetic resonance system were omitted for reasons of clarity.

Figure 2:
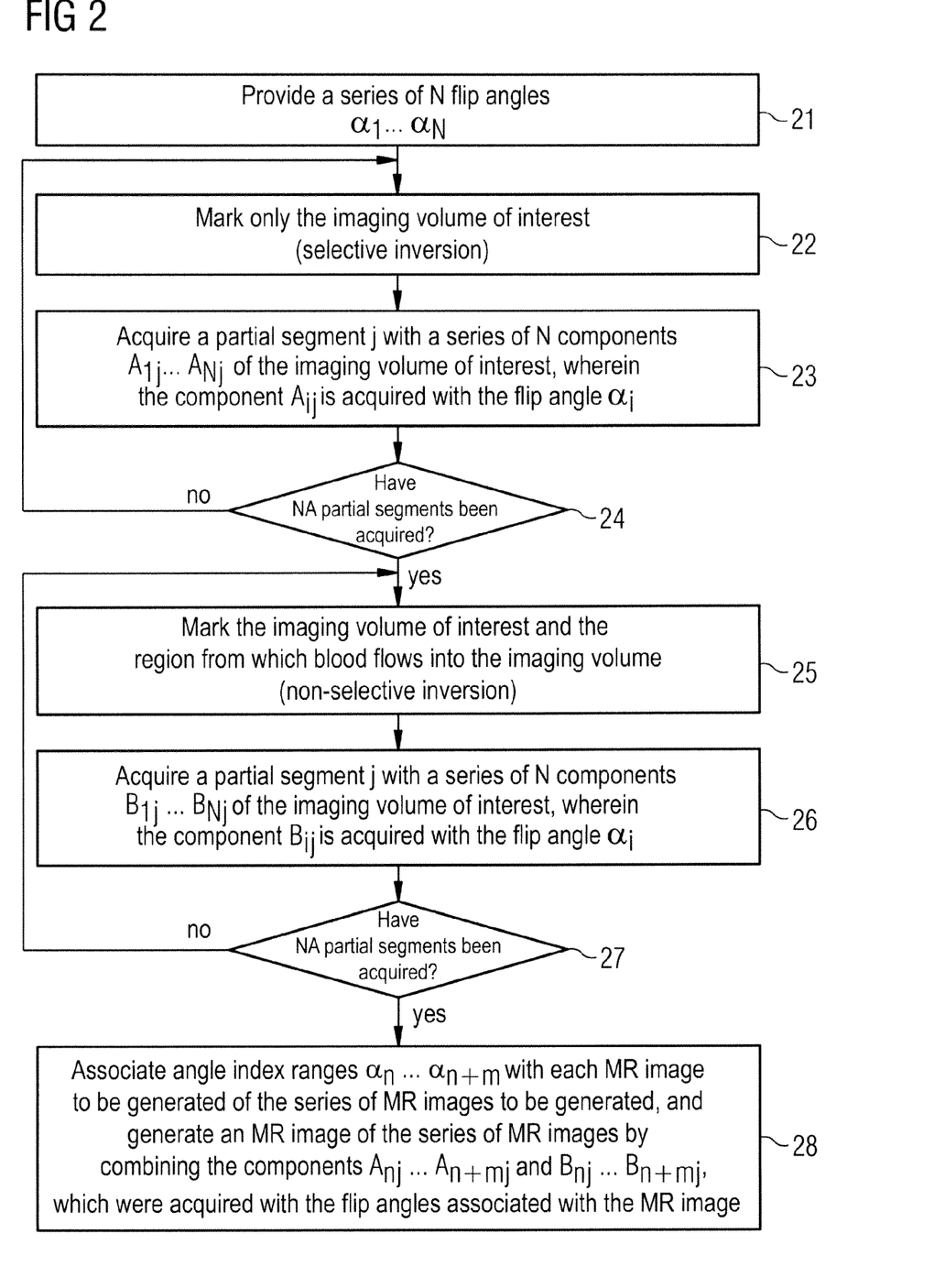
FIG. 2 shows a workflow diagram with the steps to generate the series of temporally successive angiographic magnetic resonance images.

FIG. 2 shows a workflow diagram which shows the steps according to one embodiment of the present invention that lead to the improvement of a series of temporally successive angiographic magnetic resonance images. In the workflow diagram of FIG. 2, to mask the background what is known as a FAIR method is used in which, to mask the background, one measurement is conducted after a selective inversion of the imaging volume of interest and an additional measurement is conducted after a non-selective inversion. However, the FAIR method which is used—which is described in detail in the article by Seong-Gi Kim with the title "Quantification of Relative Cerebral Blood Flow Change by Flow-Sensitive Alternating Inversion Recovery (FAIR) Technique: Application to Functional Mapping" (published in Magnetic Resonance in Medicine 34: 293-301 (1995))—is only an example and can be replaced with an arbitrary different method to mask the background. An additional method to mask the background is described by Robert R. Edelmann et al. in the article "Signal Targeting with Alternating Radio Frequency (STAR) Sequences: Application to MR Angiography" (published in Magnetic Resonance in Medicine 31: 233-238 (1994)), for example. In the following an overview of the method according to the invention is presented in connection with FIG. 2-4. A detailed explanation of the method and a comparison with existing methods is provided in the following in connection with FIGS. 5-12.

In the method shown in FIG. 2, N flip angles $\alpha_1$-$\alpha_N$ are initially established in Step 21. As will be explained in the following, the flip angles $\alpha$ are used in acquisitions of magnetic resonance data according to a gradient echo method to adjust the radio-frequency pulses. Temporally successive magnetic resonance data are generated for a predetermined time interval, wherein temporally successive data are acquired with different flip angles. For example, in a cardiac examination the predetermined time interval can amount to approximately one second and be synchronized with the heartbeat of the patient. For example, the flip angle $\alpha_1$ for the chronologically first magnetic resonance data to be acquired has a value in a range from 10-20° (for example 12°). For example, the last flip angles $\alpha_N$ for the chronologically last magnetic resonance data to be acquired has a value in a range from 30-60° (for example 45°). The interposed flip angles $\alpha_i$ increase monotonically from the value of $\alpha_1$ to the value $\alpha_N$.

Figure 3:
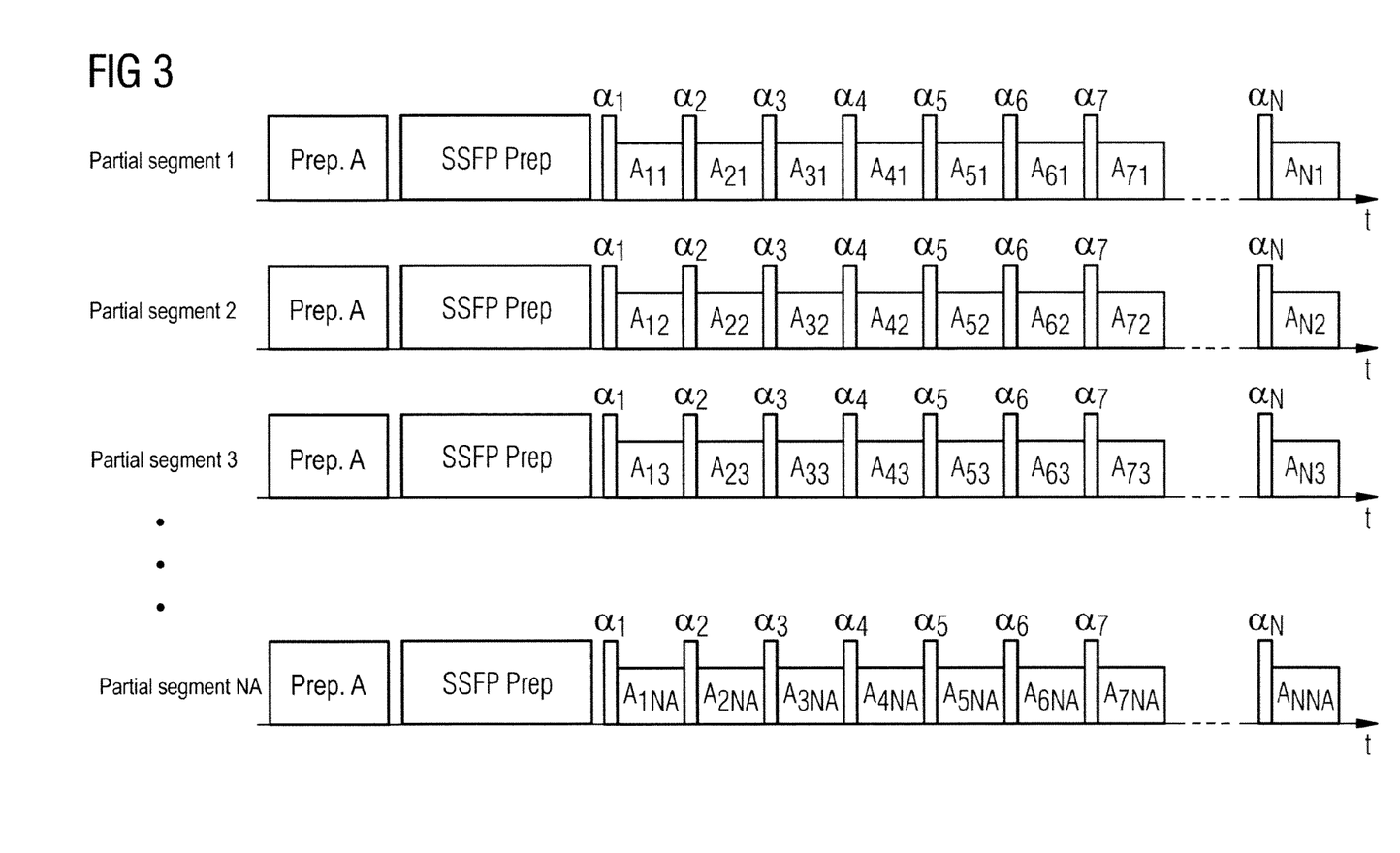
FIG. 3 schematically shows an acquisition of partial segments for first magnetic resonance data according to one embodiment of the present invention.

In Steps 22-24, first magnetic resonance data A are acquired with the aid of by a segmented acquisition in NA partial segments. Each partial segment delivers a portion of k-space data for the first magnetic resonance data A or the entire predetermined time interval, meaning that a partial segment comprises temporally successive magnetic resonance data that are acquired in N groups or components over the time interval with N flip angles. A component $A_{ij}$ of the j-th partial segment is acquired with the flip angle $\alpha_i$. N components $A_{1j}$-$A_{Nj}$ for the partial segment i are thus acquired. Before each acquisition of a partial segment, in Step 22 a selective inversion of the imaging volume of interest is implemented, meaning that the entire imaging volume of interest receives a spin marking (what is known as a spin labeling). One partial segment j of the in total NA partial segments to be acquired is then acquired in Step 23. In Step 24 it is checked whether all NA partial segments have already been acquired, and Steps 22-24 are repeated until all NA partial segments are acquired. In FIG. 3 the acquisition of the NA partial segments is shown in detail for the first magnetic resonance data A. For each acquisition of a partial segment of the NA partial segments, a selective inversion of the imaging volume of interest is implemented (Prep. A). After an optional SSFP preparation (in particular of importance for TrueFISP), the components $A_{1j}$-$A_{Nj}$ of the j-th partial segment are acquired with the flip angles $\alpha_1$-$\alpha_N$ according to a gradient echo method (for example FLASH or TrueFISP). The components $A_{1j}$-$A_{Nj}$ of the j-th partial segment are thus acquired in chronological succession with monotonically increasing flip angles. This is conducted in order for all NA partial segments.

Figure 4:
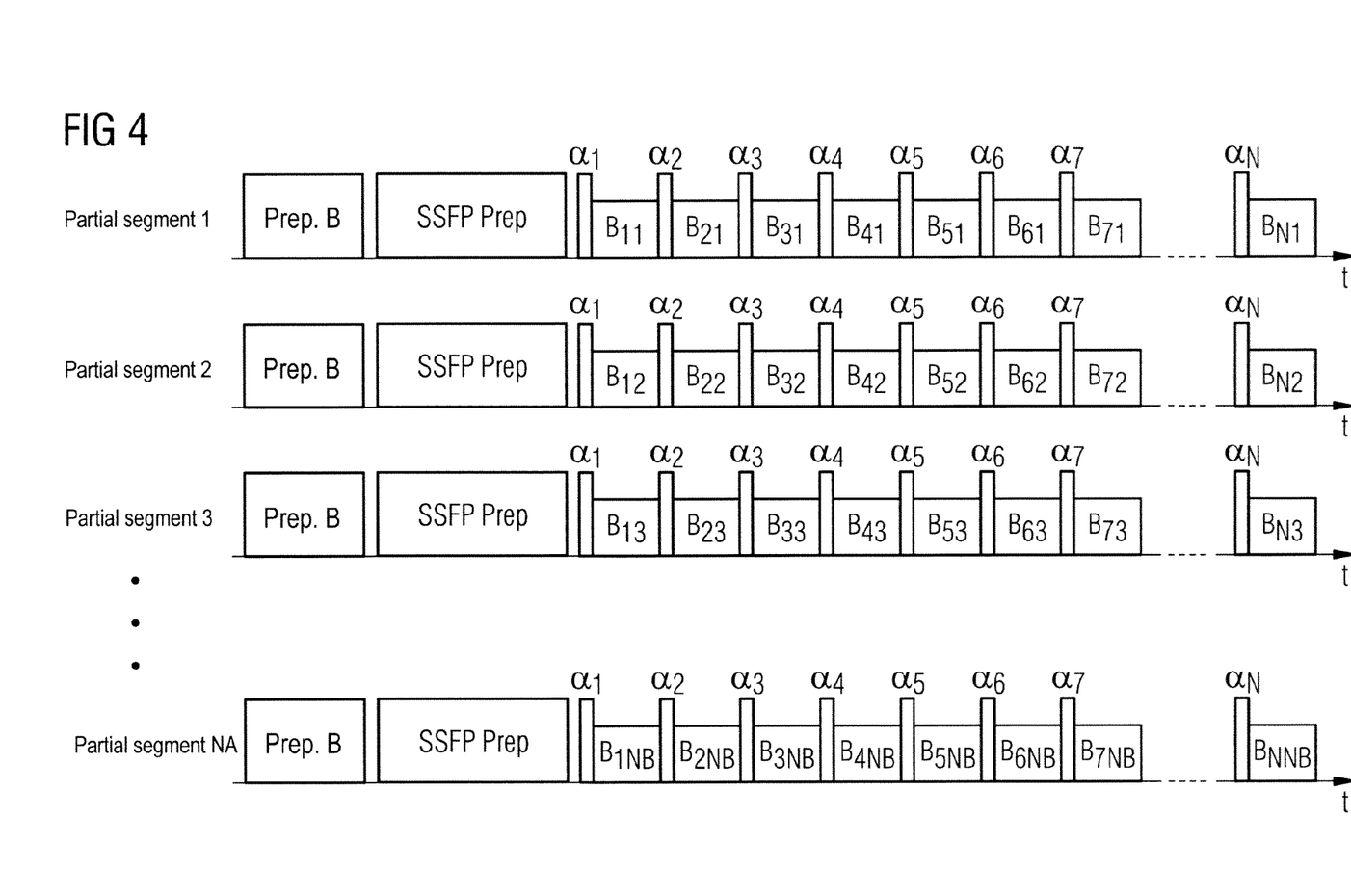
FIG. 4 schematically shows an acquisition of partial segments for second magnetic resonance data according to an embodiment of the present invention.

In Steps 25-27 of FIG. 2, second magnetic resonance data B are acquired in a similar manner with the aid of a segmented acquisition in NB partial segments. The number of partial segments NA and the number of partial segments NB are typically the same. Each partial segment delivers a portion of k-space data for the second magnetic resonance data B for the entire predetermined time interval. A component $B_{ij}$ of the j-th partial segment is acquired with the flip angle $\alpha_i$. N components $B_{1j}$-$B_{Nj}$ for the partial segment j are thus acquired. Before every acquisition of a partial segment is implemented in Step 25 of a non-selective inversion, meaning that both the imaging volume of interest and regions outside of the imaging volume of interest are provided with a spin labeling. A region outside of the imaging volume of interest is thereby in particular provided with a spin labeling, from which region a fluid (for example blood) flows into the imaging volume of interest. A partial segment j of the in total NB partial segments to be acquired is then acquired in Step 26. Whether all NB partial segments have already been acquired is checked in Step 27, and Steps 25-27 are repeated until all NB partial segments have been acquired. In FIG. 4 the acquisition of the partial segments is shown in detail for the second magnetic resonance data B. For each acquisition of a partial segment of the NB partial segments, a non-selective inversion is conducted (Prep. B). After an optional SSFP preparation (in particular of importance for TrueFISP), the components $B_{1j}$-$B_{Nj}$ of the j-th partial segment are acquired with the flip angles $\alpha_1$-$\alpha_N$ according to a gradient echo method (for example FLASH or TrueFISP). The components $B_{1j}$-$B_{Nj}$ of the j-th partial segment are thus acquired in chronological succession with monotonically increasing flip angles. This is conducted in order for all NB partial segments.

In Step 28 of FIG. 2, a series of angiographic magnetic resonance images is then generated from the first and second magnetic resonance data A,B. For this a first series of magnetic resonance images is initially generated according to the following from the first magnetic resonance data A, for example, and a second series of magnetic resonance images is generated according to the following from the second magnetic resonance data B. To generate a magnetic resonance image, a portion of the components of the partial segments of the corresponding magnetic resonance data is transformed into image space. The portion of the components is defined over a flip angle index range which is associated with the magnetic resonance image.

This procedure is explained more precisely in the following in an example. For example, 300 components with 300 flip angles are acquired per partial segment over a time interval of 900 ms. The components $A_{1j}$-$A_{300j}$ are thus generated for the partial segment j of the first magnetic resonance data A. For example, 20 components of each of the NA partial segments are respectively used to generate a magnetic resonance image, whereby a series of 15 magnetic resonance images is determined. To determine the first magnetic resonance image, the components $A_{1,1}$-$A_{20,1}$, $A_{1,2}$-$A_{20,2}$, ... $A_{1,NA}$-$A_{20,NA}$ are used and transformed into image space. To determine the second magnetic resonance image, the components $A_{21,1}$-$A_{40,1}$, $A_{21,2}$-$A_{40,2}$, ... $A_{21,NA}$-$A_{40,NA}$ are used and transformed into image space etc. In this example 15 magnetic resonance images are generated from the second magnetic resonance data B in the same manner. Thus a first series of 15 magnetic resonance images is generated from the first magnetic resonance data A and a second series of 15 magnetic resonance images is generated from the second magnetic resonance data B. Finally, difference images are generated in that respectively the corresponding differences from the magnetic resonance images of the first and second series are calculated. This means that a difference image is calculated from the corresponding magnetic resonance image of the first series and the corresponding magnetic resonance image of the second series.

The previously described method to generate the difference images is only an example, and additional methods can be used. For example, the magnetic resonance images from the first and second magnetic resonance data A,B can be generated with the use of what is known as a "view sharing" method, in which the components of the partial segments, "overlapping" partially, are used to generate the magnetic resonance images. For example, the components $A_{1,1}$-$A_{30,1}$, $A_{1,2}$-$A_{30,2}$, ... $A_{1,NA}$-$A_{30,NA}$ can be used to determine the first magnetic resonance image and be transformed into image space, and the components $A_{21,1}$-$A_{50,1}$, $A_{21,2}$-$A_{50,2}$, . . . $A_{21,NA}$-$A_{50,NA}$ can be used to determine the second magnetic resonance image and be transformed into image space etc., such that some components of two magnetic resonance images are always used in common. In an additional possible method, the components have already been complexly subtracted from one another in k-space and the differences are transformed into image space. There is yet another additional possibility to sort the components of the segments of the segments of the first and second magnetic resonance data A,B in an interleaved manner in hybrid k-space, to transform hybrid k-space into image space and to obtain the angiographic magnetic resonance images by excising a suitable partial region of image space.

In the magnetic resonance images obtained in this manner, the regions in the imaging region of interest into which no fluid or no blood flows during the acquisition of the first and second magnetic resonance data A and B are masked out due to the selective inversion of Step 22 and the non-selective inversion of Step 25. The vessels into which fluid or blood is flowing during the acquisition of the magnetic resonance data A and B show a signal in the difference image since the inflowing fluid or, respectively, the inflowing blood has no spin marking in Step 23 and has a spin marking in Step 26. A uniform signal level for the inflowing fluid or for the inflowing blood can be achieved in the difference image via the varying flip angle $\alpha$ which grows with increasing acquisition time. This will be explained in the following with reference to FIG. 5-12.

Given a continuous scanning of an inflow process—for example as is required given a generation of a series of temporally successive angiography magnetic resonance images—the temporal development of the magnetization which is used by (for example) a spin labeling according to the STAR or FAIR method is significantly affected by the continuously active measurement, and therefore the measurement signal is also significantly affected. The labeling—and thus also the difference between the signal values of inflowing blood in the two partial measurements—disappears with time, such that the blood signal in the difference images is always weaker. Vessels that only fill late after the labeling are thereby not shown. Given an implementation of a magnetic resonance angiography without contrast agent in a conventional manner—i.e. with constant flip angle—the duration of the labeling depends on many factors.

Figure 5:
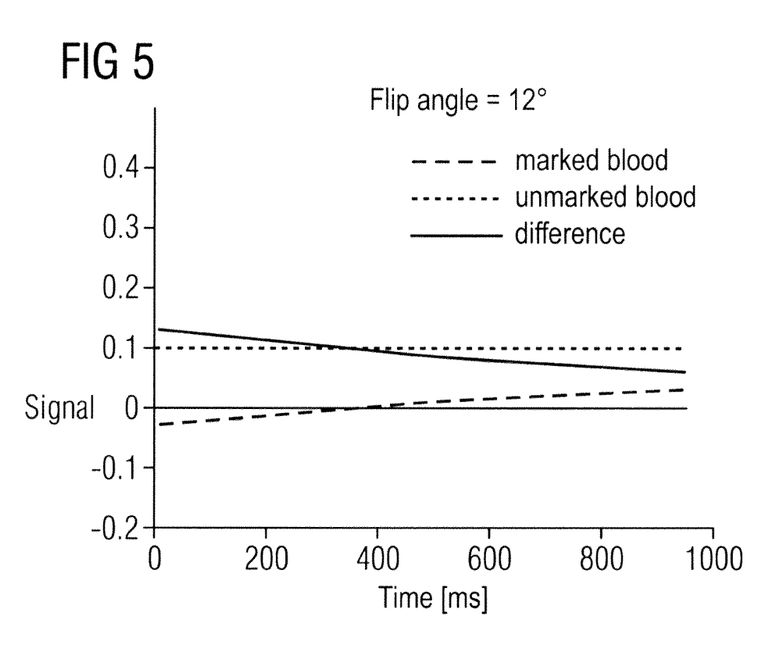
FIG. 5-8 show signal curves of marked blood and unmarked blood given magnetic resonance angiography according to the prior art.
Figure 6:
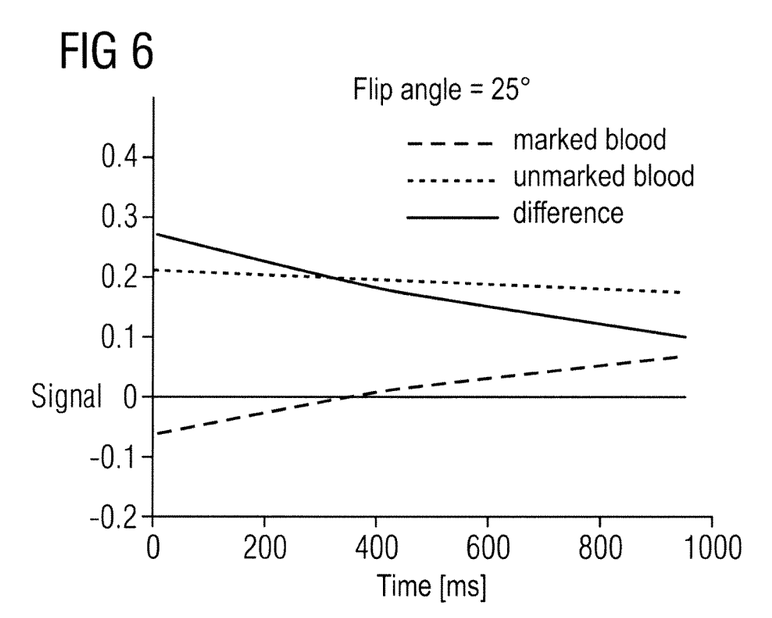
Figure 7:
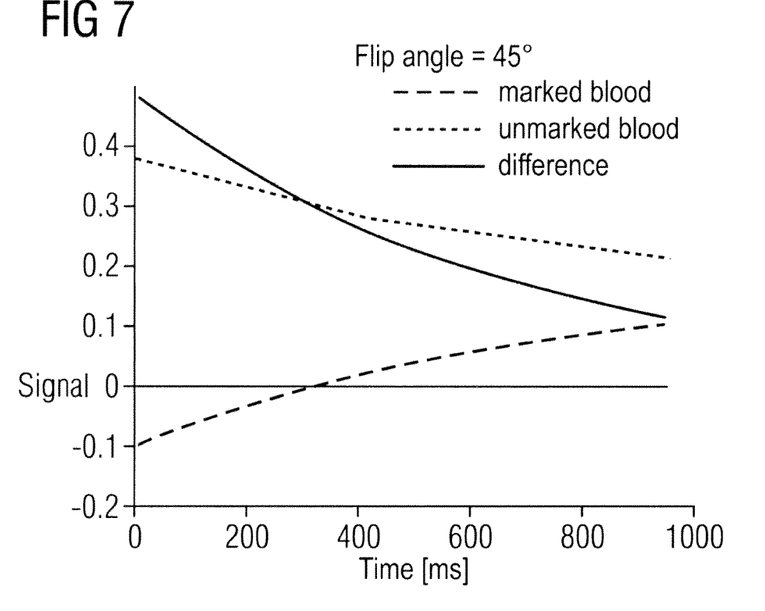
Figure 8:
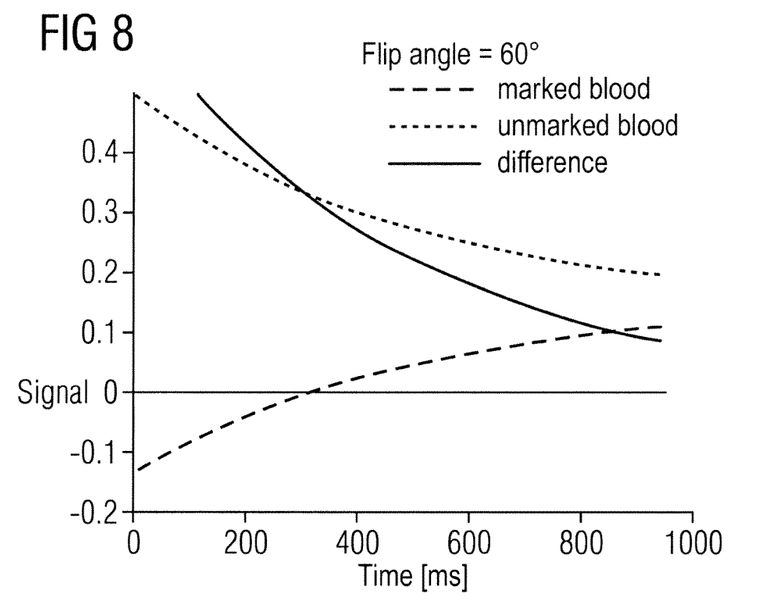

For a more precise examination, the behavior of the magnetization was simulated on the basis of Bloch equations, here for the case of a data acquisition with a TrueFISP sequence. Typical literature values given 3 T (1390 ms and 163 ms) were used for T1 and T2 of blood. The simulated measurement duration was 950 ms. For both magnetic resonance exposure—i.e. with spin labeling of the inflowing blood (marked blood) and without spin labeling of the inflowing blood (unmarked blood)—the signal curve of arterial blood that flows directly into the examination region of interest after the inversion was examined because, as expected, this will cover the farthest path within the examination region of interest during the acquisition of the magnetic resonance images. In the acquisition after slice-selective inversion it was assumed that newly arriving blood flows in a magnetic steady state. In the case of non-selective inversion it was assumed that the blood outside of the examination region of interest has already experienced inversions of four preceding measurement durations. In addition to the respective signals for blood, a phase-sensitive difference signal was calculated which corresponds to the separation of the two curves for the marked blood and the unmarked blood. FIG. 5 shows the simulated signal curve with constant, low flip angle of 12°. At this flip angle what is known as the steady state signal is primarily very low, and the difference is also very small starting from a quite small initial signal. FIG. 6-8 show additional signal simulations with flip angles 25°, 45° or, respectively, 60°. Although with increasing flip angles an increasingly high signal is generated directly after the inversion and the signal of blood approaches a higher steady state value, this process takes place with time constants that grow increasingly shorter, which disadvantageously affects the duration of the labeling. In all cases, the difference signal for blood is falling monotonically.

Figure 9:
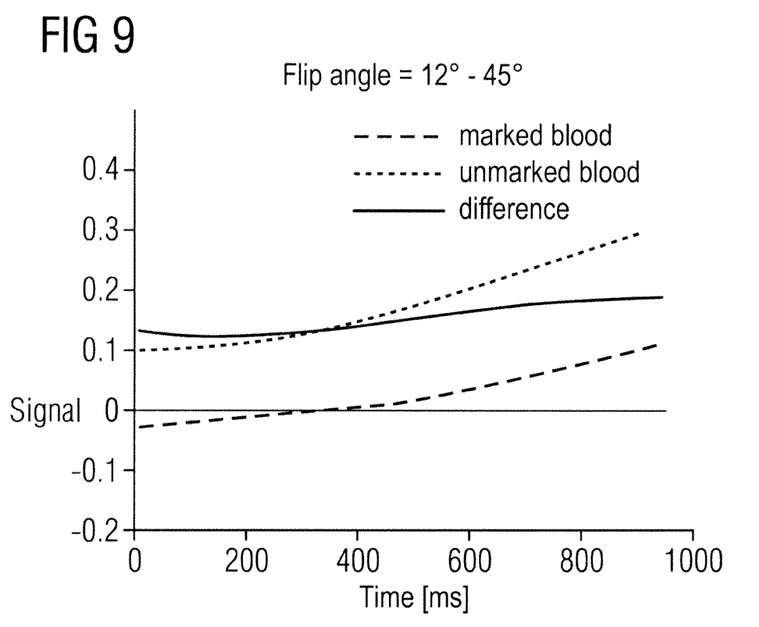
FIG. 9 shows a signal curve of marked blood and unmarked blood in magnetic resonance angiography according to an embodiment of the present invention.

In the method described in connection with FIG. 2, a variable flip angle is therefore used. The reason for this is that, directly after the spin labeling, the large magnitude of the freshly inflowing magnetization can be utilized, whereby a relatively small flip angle is sufficient in order to obtain sufficient signal. A small flip angle accompanies a large effective time constant, meaning that the relaxation time runs quite close to true T1 so that due to the measurement the relaxation is comparably less additionally accelerated, and thus a greater difference is maintained between inverted and non-inverted longitudinal magnetization. At a later point in time in the labeling interval, larger flip angles are used in order to move the development of the magnetization in the direction of an optimally high steady state value. A sufficiently large signal can thereby also be obtained at the end of the acquisition interval. A quadratic correlation for a rise (slope) of the flip angle over the acquisition interval is particularly suitable in order to obtain a suitable and high signal difference over a long period of time and to simultaneously deliver sufficient signal directly after the inversion. For example, the flip angle $\alpha_i$ for the i-th radio-frequency pulse (of N radio-frequency pulses in total) can be calculated as follows:

$$\alpha_i = \alpha_1 + (\alpha_N - \alpha_1) \times (i/N)^2,$$

wherein $\alpha_1$ and $\alpha_N$ are the first and the last flip angles, respectively. FIG. 9 shows a corresponding signal curve of marked blood and unmarked blood with flip angles in a range from 12°-45°, i.e. $\alpha_1 = 12°$ and $\alpha_N = 45°$. The difference signal that results (which difference signal is likewise shown in FIG. 9) is essentially constant across the observation time period. A blood signal at the end of the time interval can be established with the flip angle curve from 12°-45°, which is higher by a factor of 1.5-2 than that of a signal with constant flip angle.

Figure 10:
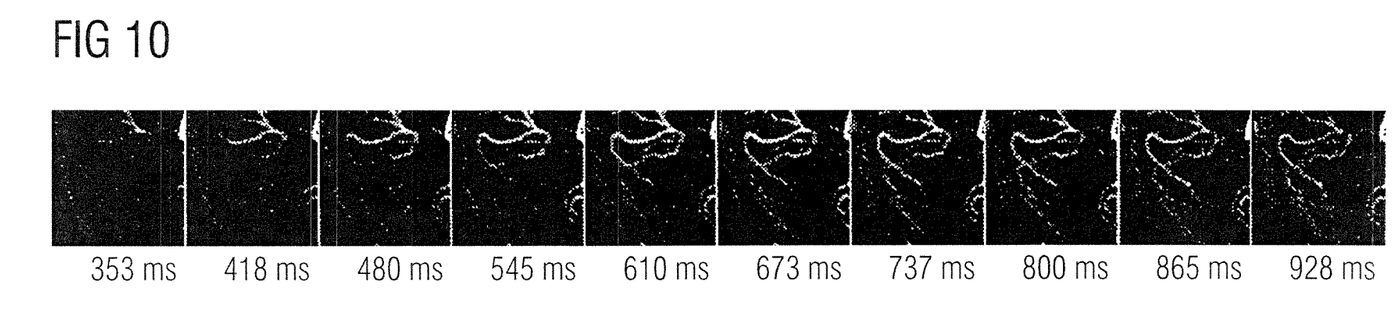
FIG. 10 shows a series of temporally successive angiographic magnetic resonance images according to the prior art.
Figure 11:
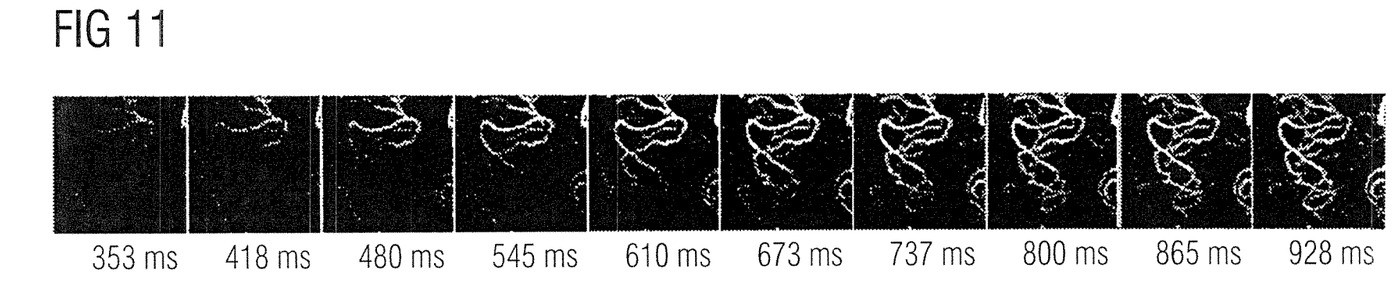
FIG. 11 shows a series of temporally successive angiographic magnetic resonance images according to one embodiment of the present invention.

FIG. 10 shows an MIP representation of ten temporally successive angiography magnetic resonance images of an examination volume at ten points in time between 353 ms and 928 ms (within a predetermined time interval which is synchronized with a heartbeat of an examination subject, for example). The angiographic magnetic resonance images of FIG. 10 were acquired with a constant flip angle of 25°. FIG. 11 shows the same examination volume in ten MIP representations of angiographic magnetic resonance images that were acquired as described before with different flip angles in a range from 12-45°. As is apparent from a comparison of FIGS. 10 and 11, significant improvements could be achieved, in particular in vessels that the inflowing blood only reaches 600 ms or later after the labeling. The ratio between the signal of late-filling vessels and the background signal thereby increases by factors between 1.44 and 1.87. A markedly longer presence of the labeling and a better depiction of the vessels can thus be achieved with the variable flip angle.

Figure 12:
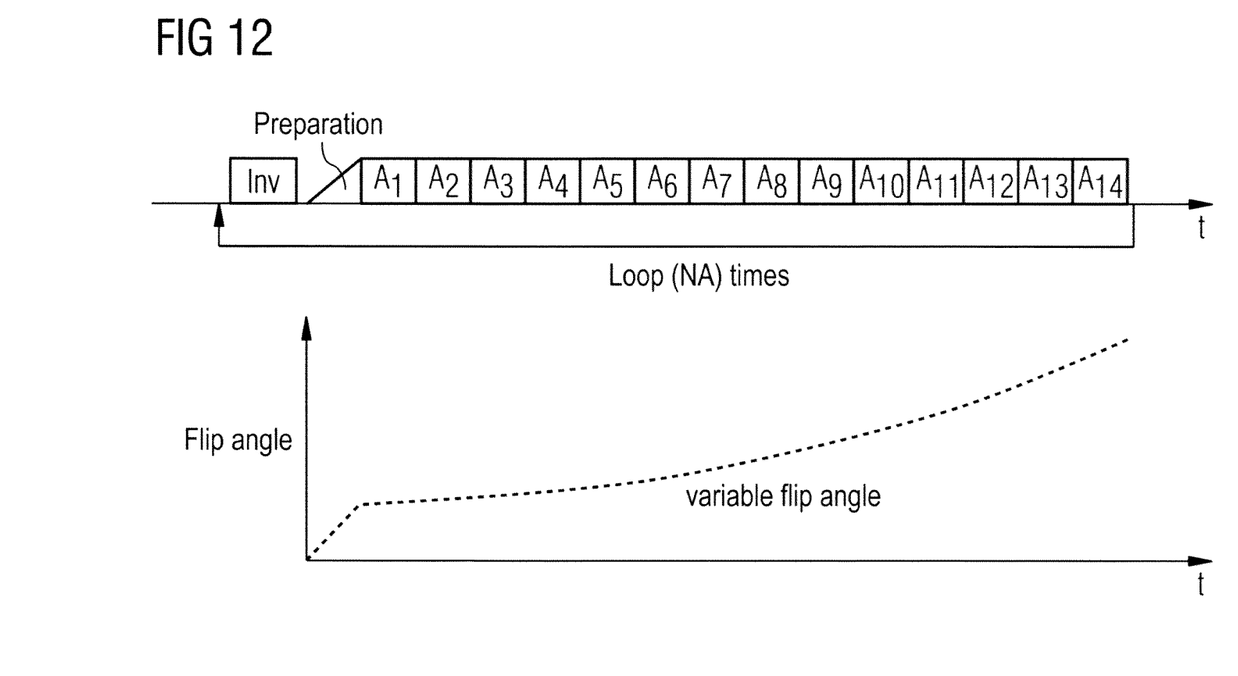
FIG. 12 schematically shows a workflow of the method to generate a series of temporally successive angiographic magnetic resonance images according to one embodiment of the present invention.

In FIG. 12 the acquisition method is shown in an example of an individual data set, thus for example to generate the magnetic resonance images from the first magnetic resonance data A. After the inversion (Inv) (which is shown generically in FIG. 12 and which is conducted once selectively and once non-selectively as described in connection with FIG. 2), an SSFP preparation (Preparation) for the first flip angle $\alpha_1$ can optionally be implemented for the first flip angle $\alpha_1$. This can be a series of so-called dummy excitations, for example with linearly increasing flip angle ramp for the first flip angle $\alpha_1$. In the individual case this preparation (Preparation) could also be executed differently, for example via a single pulse at an interval TR/2 before the first following excitation and half flip angle of the following first excitation pulse.

An acquisition of magnetic resonance data for fourteen magnetic resonance images $TA_1$-$TA_{14}$ follows this. The individual magnetic resonance images $TA_1$-$TA_{14}$ can also be acquired in segments as described previously, meaning that NA segments (k-space lines) are acquired for each magnetic resonance image. Thus NA is selected based on the usual considerations relating to the selection of the number of k-space lines that will be used to form an MR image, such as image quality or a processing limitation on the number of k-space lines. For this the entire loop must be repeated NA times until all data are provided. The flip angle $\alpha$ is varied during the acquisition of the segments from smaller to greater flip angle. The previously described quadratic correlation is shown as an example in FIG. 12; however, other curves are also possible, for example a linearly increasing curve or an initially constant curve and then an increasing curve.

Although modifications and changes may be suggested by those skilled in the art, it is the intention of the inventor to embody within the patent warranted hereon all changes and modifications as reasonably and properly come within the scope of his contribution to the art.

I claim as my invention:

1. Method to generate an image series comprising a predetermined first number of temporally successive angiographic magnetic resonance images of an examination region of a subject, said method comprising:
    establishing a flip angle series comprising a predetermined second number of flip angles, wherein the first flip angle at the beginning of the flip angle series is smaller than the last flip angle at the end of the flip angle series, and wherein an arbitrary flip angle is greater than the preceding flip angle in the flip angle series;
    operating a magnetic resonance data acquisition unit according to a gradient echo sequence that includes excitation of nuclear spins in said examination region with radio-frequency pulses respectively having flip angles in said flip angle series, to acquire first magnetic resonance data, and entering said first magnetic resonance data into a predetermined third number of first regions of k-space, reserved for the first magnetic resonance data, with each first region comprising first magnetic resonance data acquired during respective first time intervals and each first region comprising a plurality of components equal to said second number, with each component in each first region being acquired according to said gradient echo sequence with a respective flip angle that exists at a position in the flip angle series that gives at a beginning of each first time interval, a fluid flowing into the examination region a first predetermined spin marking;
    operating said magnetic resonance data acquisition unit according to said gradient echo sequence to acquire second magnetic resonance data, and entering said second magnetic resonance data into a predetermined fourth number of second regions of k-space, reserved for the second magnetic resonance data, with each second region comprising second magnetic resonance data acquired during respective second time intervals and each second region comprising a plurality of components equal to said second number, with each component in each second region being acquired according to said gradient echo sequence with a respective flip angle that exists at a position in the flip angle series that gives, at a beginning of each second time interval, said fluid flowing into the examination region a second predetermined spin marking that is different than the first spin marking;
    establishing contiguous flip angle index ranges for each angiographic magnetic resonance image in said image series;
    in a processor, generating each angiographic magnetic resonance image of the examination region in said image series as a difference image formed between a portion of the first magnetic resonance data and a portion of the second magnetic resonance data, the portion of the first magnetic resonance data comprising components of the third number of first regions that were acquired with flip angles in the flip angle index range established for that respective angiographic magnetic resonance image, and the portion of the second magnetic resonance data comprising components of the fourth number of second regions that were acquired with flip angles in the flip angle index range established for that respective angiographic magnetic resonance image; and
    making the angiographic magnetic resonance images in said image series available in electronic form at an output of said processor.

2. Method according to claim 1, wherein the predetermined third number of first regions is equal to the predetermined fourth number of second regions.

3. Method according to claim 1, comprising acquiring the first magnetic resonance data in the predetermined third number of first regions temporally interleaved with acquiring the second magnetic resonance data in the predetermined fourth number of second regions.

4. Method according to claim 1, wherein the predetermined number is one, so a totality of said first magnetic resonance data are acquired in only one first time interval and wherein said predetermined fourth number is one, so a totality of said second magnetic resonance data are acquired in only one second time interval.

5. Method according to claim 1, comprising generating each difference image by:
    transforming the portion of the first magnetic resonance data from said first k-space into image space in order to obtain a first magnetic resonance image;
    transforming the portion of the second magnetic resonance data from said second k-space into image space in order to obtain a second magnetic resonance image; and
    forming said difference image as a difference between the first magnetic resonance image and the second magnetic resonance image.

6. Method according to claim 1, comprising generating each difference image by:
    performing a complex subtraction of the portion of the first magnetic resonance data in said first k-space and the portion of the second magnetic resonance data in said second k-space, to obtain subtracted k-space data;
    transforming the subtracted k-space data from k-space into image space; and
    forming the difference image from the subtracted k-space data transformed into image space.

7. Method according to claim 1, comprising synchronizing the first and the second time intervals with heartbeats of the subject.

8. Method according to claim 1, comprising selecting the gradient echo sequence from the group consisting of a FLASH gradient echo sequence and a TrueFISP gradient echo sequence.

9. Method according to claim 1, comprising displaying the temporally successive angiography magnetic resonance images using an MIP depiction.

10. Method according to claim 1, comprising temporally contiguously acquiring the first magnetic resonance data in said third number of first regions, and temporally contiguously acquiring said second magnetic resonance data in said predetermined fourth number of second regions before or after acquiring said first magnetic resonance data.

11. Method according to claim 1 comprising acquiring said first magnetic resonance data as a three-dimensional data set and acquiring said second magnetic resonance data as a further three-dimensional data set, and generating each of said angiographic magnetic resonance images in said image series as a three-dimensional image.

12. Method according to claim 1 comprising acquiring said first magnetic resonance data as a two-dimensional data set and acquiring said second magnetic resonance data as a further two-dimensional data set, and generating each of said angiographic magnetic resonance images in said image series as a two-dimensional image.

13. Method according to claim 1 comprising entering said first magnetic resonance data into k-space reserved for said first magnetic resonance data according to a non-Cartesian trajectory, and entering said second magnetic resonance data into k-space reserved for said second magnetic resonance data along a non-Cartesian trajectory.

14. Method as claimed in claim 1 comprising setting a value of each flip angle in said flip angle series according to a quadratic curve that relates respective flip angle values to respective positions of the flip angles in said flip angle series.

15. A magnetic resonance system comprising:
a magnetic resonance data acquisition unit adapted to interact with a subject to acquire magnetic resonance data from an examination region of the subject, as a predetermined first number of angiographic magnetic resonance images, in an image series, of the examination subject;
a computerized control unit supplied with an operating protocol comprising a gradient echo sequence comprising radio-frequency pulses respectively having flip angles in a flip angle series comprising a predetermined second number of flip angles, wherein the first flip angle at the beginning of the flip angle series is smaller than the last flip angle at the end of the flip angle series, and wherein an arbitrary flip angle is greater than the preceding flip angle in the flip angle series;
said control unit being configured to operate the data acquisition unit according to the protocol to acquire first magnetic resonance data, and to enter said first magnetic resonance data into a predetermined third number of first regions of k-space, reserved for the first magnetic resonance data, with each first region comprising first magnetic resonance data acquired during respective first time intervals and each first region comprising a plurality of components equal to said second number with each component in each first region being acquired according to said gradient echo sequence with a respective flip angle that exists at a position in the flip angle series that gives, at a beginning of each first time interval, a fluid flowing into the examination region a first predetermined spin marking;
said control unit being configured to operate the data acquisition unit according to the protocol to acquire second magnetic resonance data, and to enter said second magnetic resonance data into a predetermined fourth number of second regions of k-space, reserved for the second magnetic resonance data, with each second regions comprising second magnetic resonance data acquired during respective second time intervals and each second region comprising a plurality of components equal to said second number, with each component in each second region being acquired according to said gradient echo sequence with a respective flip angle that exists at a position in the flip angle series that gives, at a beginning of each second time interval, said fluid flowing into the examination region a second predetermined spin marking that is different than the first spin marking;
said control unit being configured to establish contiguous flip angle index ranges for each angiographic magnetic resonance image in said image series;
a computerized processor supplied with the first magnetic resonance data and the second magnetic resonance data, said processor being configured to generate each angiographic magnetic resonance image of the examination region in said image series as a difference image formed between a portion of the first magnetic resonance data and a portion of the second magnetic resonance data, the portion of the first magnetic resonance data comprising components of the third number of first regions that were acquired with flip angles in the flip angle index range established for that respective angiographic magnetic resonance image, and the portion of the second magnetic resonance data comprising components of the fourth number of second regions that were acquired with flip angles in the flip angle index range established for that respective angiographic magnetic resonance image; and
said processor being configured to make the angiographic magnetic resonance images in said image series available in electronic form at an output of said processor.

16. A non-transitory computer-readable storage medium encoded with programming instructions, said storage medium being loaded into a computerized control and processing system of a magnetic resonance system, said magnetic resonance system also comprising a magnetic resonance data acquisition unit adapted to interact with a subject to acquire magnetic resonance data from an examination region of the subject in order to generate an image series comprising a predetermined first number of temporally successive angiographic magnetic resonance images of the examination region of the subject, said programming instructions causing said control and processing system to:
establish a flip angle series comprising a predetermined second number of flip angles, wherein the first flip angle at the beginning of the flip angle series is smaller than the last flip angle at the end of the flip angle series, and wherein an arbitrary flip angle is greater than the preceding flip angle in the flip angle series;
operate the data acquisition unit according to a gradient echo sequence that includes excitation of nuclear spins in said examination region with radio-frequency pulses respectively having flip angles in said flip angle series, to acquire first magnetic resonance data and to enter said first magnetic resonance data into a predetermined third number of first regions of k-space, reserved for the first magnetic resonance data, with each first region comprising first magnetic resonance data acquired during respective first time intervals and each first region comprising a plurality of components equal to said second number, with each component in each first region being acquired according to said gradient echo sequence method with a respective flip angle that exists at a position in the flip angle series that gives, at a beginning of the first time intervals, a fluid flowing into the examination region a first predetermined spin marking;

operate the data acquisition unit according to said gradient echo sequence to acquire second magnetic resonance data and to enter said second magnetic resonance data into a predetermined fourth number of second regions of k-space, reserved for the second magnetic resonance data, with each second region comprising second magnetic resonance data acquired during respective second time intervals and each second region comprising a plurality of components equal to said second number, with each component in each second region being acquired according to said gradient echo sequence with a respective flip angle that exists at a position in the flip angle series that gives, at a beginning of each second time interval, said fluid flowing into the examination region a second predetermined spin marking that is different than the first spin marking;

establish contiguous flip angle index ranges for each angiographic magnetic resonance image in said image series;

generate each angiographic magnetic resonance image of the examination region in said image series as a difference image formed between a portion of the first magnetic resonance data and a portion of the second magnetic resonance data, the portion of the first magnetic resonance data comprising components of the third number of first regions that were acquired with flip angles in the flip angle index range established for that respective angiographic magnetic resonance image, and the portion of the second magnetic resonance data comprising components of the fourth number of second regions that were acquired with flip angles in the flip angle index range established for that respective angiographic magnetic resonance image; and make the angiographic magnetic resonance images in said image series available in electronic form at an output of said processor.

\* \* \* \* \*